US00PP14347P39

(12) United States Plant Patent
Malone et al.

(10) Patent No.: US PP14,347 P3
(45) Date of Patent: Dec. 2, 2003

(54) PEACH TREE NAMED "SOUTHERN STAR"

(50) Latin Name: *Prunus persica*
Varietal Denomination: Southern Star

(75) Inventors: Michael T Malone, Havelock North (NZ); Paul G Glucina, Auckland (NZ)

(73) Assignee: The Horticulture and Food Research Institute of New Zealand, Limited, Palmerston North (NZ)

( * ) Notice: Subject to any disclaimer, the term of this patent is extended or adjusted under 35 U.S.C. 154(b) by 0 days.

(21) Appl. No.: 10/170,218

(22) Filed: Jun. 10, 2002

(65) Prior Publication Data

US 2003/0009797 P1 Jan. 9, 2003

(51) Int. Cl.[7] ..... A01H 5/00

(52) U.S. Cl. ..... Plt./195

(58) Field of Search ..... Plt./195

*Primary Examiner*—Bruce R. Campell
*Assistant Examiner*—Susan B. McCormick
(74) *Attorney, Agent, or Firm*—Greenlee Winner and Sullivan PC

(57) ABSTRACT

A new and distinct variety of peach tree (*Prunus persica*), named 'Southern Star', is described. The new variety is a selection derived from the open pollinated seed of 'Yumyeong' (not patented) and is distinguishable from the parent variety by ripening 1 week earlier than 'Yumyeong' and having sweeter, more aromatic fruit. Its novelty consists of a unique combination of features that include late flowering, heavy and regular cropping, large, very firm, white flesh, crisp-textured, clingstone fruit with a red overcolor. Fruit have a sweet, sub-acid flavor.

2 Drawing Sheets

CROSS REFERENCE TO RELATED APPLICATIONS

This application claims benefit of New Zealand PVR Application SFM 104, filed Jun. 11, 2001.

Genus and species of plant claimed: *Prunus persica.*

BACKGROUND OF THE INVENTION

The present new and distinct variety originated from an open pollinated population of seedlings derived from the variety 'Yumyeong' (not patented) planted in 1990 at the HortResearch experimental orchard in Goddard Lane, Havelock North, New Zealand. A large group of open-pollinated seedlings on their own roots were placed under careful observation. One seedling representing the present variety was selected and asexually propagated for further evaluation. The selection was further propagated by asexual reproduction for the first time in 1995.

The new variety was budded onto 'Golden Queen' peach seedling rootstock and shows the unique combination of characteristics and distinctive color are true to the original seedling tree and are transmitted through succeeding asexual generations.

The variety is characterised by late flowering, vigorous spreading growth; regular and heavy cropping of large, very firm, white-fleshed crisp-textured fruit which are clingstone with mild and sweet sub-acid flavor and fruit aroma. The fruit is further characterised by pink color and very good handling qualities, and ripening 1 week before the parent 'Yumyeong'.

SUMMARY OF THE INVENTION

The described variety of peach tree is of a medium to large size, vigorous, with a spreading growth habit. Trees of the variety bear regular and productive crops of medium to large white flesh, clingstone fruit with a sweet sub-acid taste and very firm crisp flesh. Fruit has very good flavor and eating quality. The firm flesh exhibits good storage qualities and the skin has red color over a cream background. The fruit ripens mid season approximately 1 week before the 'Yumyeong' parent variety.

DETAILED DESCRIPTION OF THE NEW VARIETY

Figure 1:
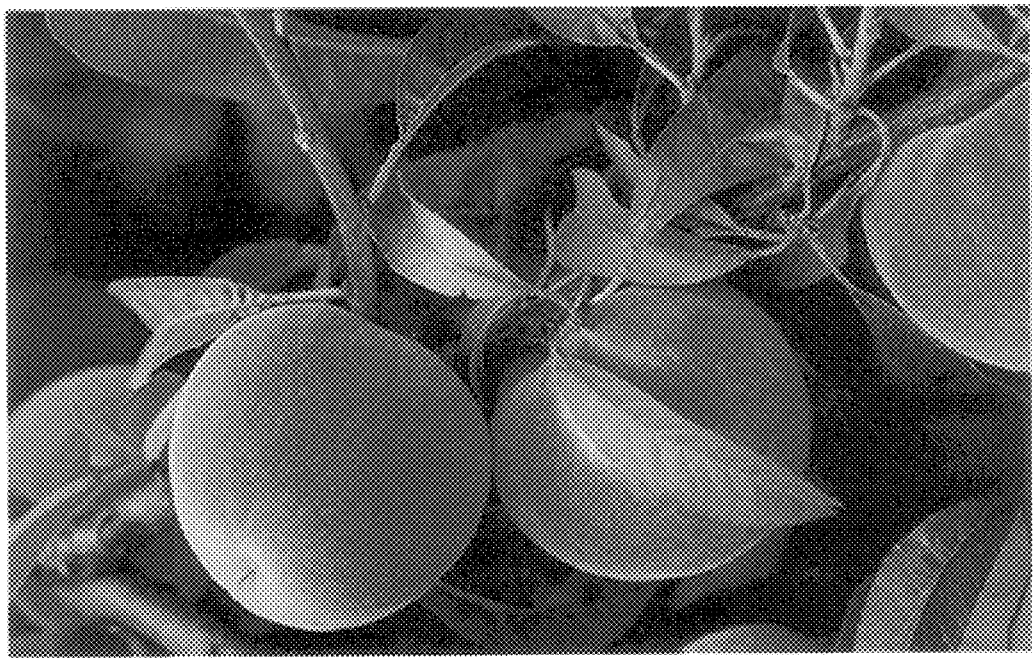
FIG. 1 shows the exterior view of the fruit on the tree at harvest.
Figure 2:
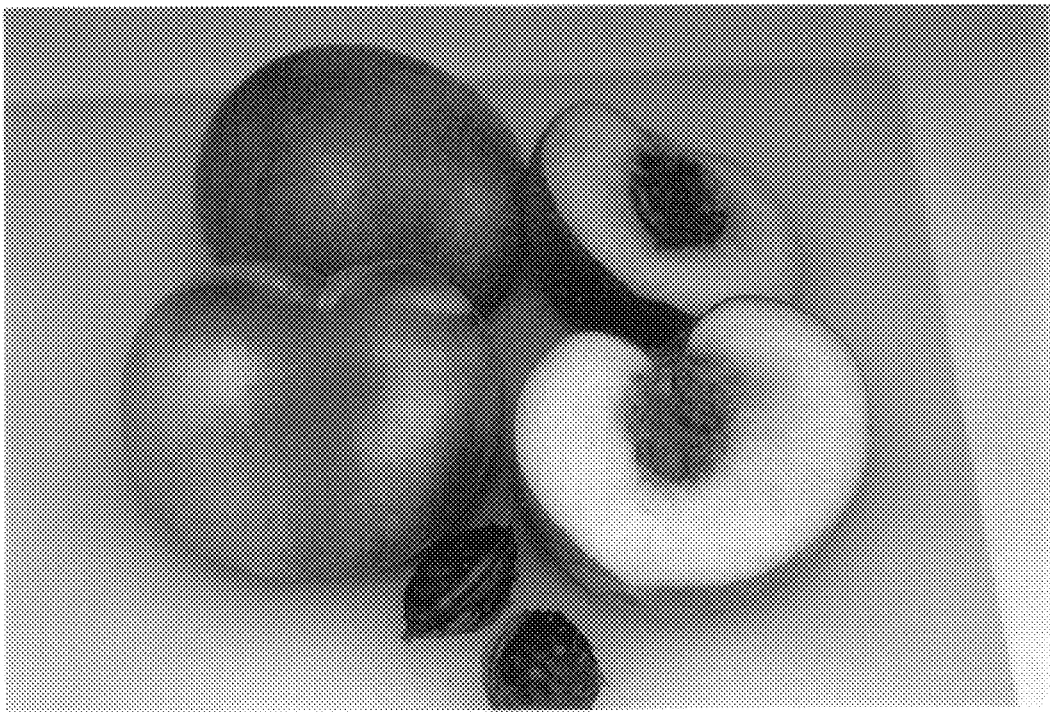
FIG. 2 shows external and internal views of the fruit. The photograph was taken after 2 weeks air storage of fruit harvested at eating maturity.

The following is a detailed description of the new variety with color terminology in accordance with The Royal Horticultural Society Colour Chart (R.H.S.C.C.) 2000 edition.

The present new variety of peach tree, the flowers, foliage and fruit herein described may vary slightly in detail due to climate, soil conditions and cultural practices under which the variety may be grown. Unless otherwise stated the present description is that of the variety grown under the environmental conditions prevailing near Havelock North, Hawke's Bay New Zealand. The observations were made in the 2001 season on trees that were four years old at the time.

Tree:

*Size.*—Large; typically a mature orchard tree is contained at approximately 3 m in height and 2.8 m in width through annual pruning.

*Vigor.*—Vigorous; young tree growth rates of approximately 600 mm increase in tree height in the first season from planting have been observed. From maturity, and one the tree has filled its allotted orchard space, annual total shoot growth has been observed to be in the range 600 mm to 1100 mm.

*Form.*—Pruned to central leader, with a spreading growing habit.

Trunk:

*Size.*—Medium; average diameter approximately 66 mm when measured 500 mm above ground level.

*Texture.*—Medium rough.

*Color.*—Grey/brown (near RHS Fan 4 197A).

Branch:

*Size.*—Medium; average diameter approximately 27 mm when measured 500 mm from the trunk.

*Texture.*—Smooth-rough.

*Lenticels.*—Large elongated shape, typically approximately 2 mm in length and 1 mm in diameter, the number varies with age of growth with a density of approximately 6 per $cm^2$being observed. Near RHS Fan 4 N170B in color.

*Color.*—Grey/brown (near RHS Fan 4 165A).

Leaves:

*Size.*—Medium to large, average width 55 mm and average length 190 mm.

*Shape.*—Lanceolate. Shape of tip acuminate, angle of tip is narrow acute, shape of the base is attenuate, incision of margin is crenate. Near RHS Fan 3 145A in color.

*Thickness.*—Medium.

*Surface.*—Smooth.

*Petiole.*—Medium length, average length 15 mm. medium thickness, the diameter being approximately 2 mm.

*Glands.*—Reniform, elongated, predominant number of nectaries on fully developed leaf more than two, average 4.

*Color.*—Upper surface dark green (RHS Fan 3 141A), lower surface lighter green (near RHS Fan 3 146B).

*Veins.*—Venation pattern, pinnate: vein color, near RHS Fan 3 154C.

Flower buds:

*Size.*—Medium to large; in dormancy typical length is approximately 4 mm, and diameter approximately 2.5 mm.

*Shape.*—Conic.

*Color.*—In dormancy bud scales are near RHS Fan 4 178A; pubescent tips are near RHS Fan 4 198D.

Flowers:

*Size.*—Medium to large; the open flower is typically in the range of approximately 40 to 45 mm in diameter.

*Inflorescence.*—Typically 3 to 4 individual flowers per cluster.

*Petals.*—Shape, round; length, approximately 18 to 20 mm; diameter, approximately 16 to 18 mm; color (both surfaces), medium pink (near RHS Fan 2 62B); texture, glabrous; margin, variable, smooth to slightly riffled and slightly cupped at apex; number per flower, five.

*Sepals.*—Number; five; approximately 5 mm, color, near RHS Fan 4 182B.

*Pubescence of ovary.*—Present.

*Reproductive organs.*—Stamens, many; filament near RHS Fan 4 155D in color prior to anthesis, darkening to near RHS Fan 1 47 B at full bloom; anther, near RHS Fan 4 184 B in color prior to anthesis; pollen, present, near RHS Fan 1 17C in color; style, one per flower.

*Fragrance.*—Present; slight.

*Blooming period.*—The trees flowered in mid-late September. Date of 5% bloom approximately September 20, full bloom September 30, 5% petal fall Oct. 7, 2000 in Havelock North, Hawkes Bay, New Zealand. Full bloom October 3 in Clyde, New Zealand.

Fruit:

*Harvest maturity.*—Fruit ripened for eating late season. Harvest usually commences about February 1 in Hawke's Bay (warm temperate region), New Zealand.

*Date first pick.*—February 1 in Havelock North, Hawkes Bay, New Zealand.

*At maturity for consumption, ripe.*—Size. Medium, average weight 170 grams. Circumference (across suture line) averages approximately 173 mm. Circumference axially approximately 164 mm.

*Shape.*—In ventral view, round oblate, symmetrical.

*Shape of pistil end.*—Rounded, slightly depressed.

*Suture.*—Shallow, extends from base to apex.

*Cavity.*—Rounded, medium to deep, average depth 9 mm, average width 28 mm.

Flesh:

*Ripen.*—Evenly.

*Texture.*—Firm non-melting.

*Fibers.*—Non fibrous.

*Aroma.*—Slight.

*Flavor.*—Good, low acid, mild.

*Soluble solids.*—Average 10–12 Brix.

*Juice.*—Moderate juicy.

*Color.*—White (near RHS Fan 4 155D).

*Anthocyanin.*—Low.

Stem:

*Size.*—Medium, average 5 mm in length.

*Color.*—Bright green (near RHS Fan 3 150C).

Skin:

*Thickness.*—Medium.

*Texture.*—Medium to strong adherence of skin to flesh.

*Pubescence.*—Sparse; pubescent.

*Tendency to crack, none.*—Color. Red (near RHS Fan 1 46A), blending to a pink (near RHS Fan 1 48A) blush pattern of over color. Cream ground color of skin (near RHS Fan 1 11D).

Stone:

*Type.*—Cling.

*Size.*—Medium, average stone length 32 mm, average stone width 26 mm, average stone thickness 17.5 mm, average stone weight 6.5 grams.

*Shape.*—In lateral view, round/elliptic.

*Surface.*—Relief of surface, pits and grooves, pitted towards the base.

*Tendency to split.*—None.

*Color.*—Brown (near RHS Fan 4 165A).

*Comparison to other known varieties.*—A comparison of the candidate with other known white fleshed, dessert peach varieties, is shown in Table 1.

TABLE 1

COMPARISON WITH OTHER VARIETIES

| Characteristic | Expression of characteristic in Southern Star | Other known variety | Expression of characteristic in other known variety |
|---|---|---|---|
| Flesh texture | Non-melting | Tasty Zee (PP6,409) | Melting |
| | | White Lady (PP5,821) | Melting |

TABLE 1-continued

COMPARISON WITH OTHER VARIETIES

| Characteristic | Expression of characteristic in Southern Star | Other known variety | Expression of characteristic in other known variety |
|---|---|---|---|
| Stone adherence | Cling | Tasty Zee (PP6,409) | Free |
| | | White Lady (PP5,821) | Free |
| Timing of maturity[1] | Late season | Tasty Zee (PP6,409) | Mid season[2] |
| | | White Lady (PP5,821) | Mid season |

[1]Fruit firm ripe; observations made under New Zealand conditions.
[2]Approximately 15th January under New Zealand conditions.

Storage: Trials indicate 2–3 weeks air storage without internal breakdown of flesh. Fruit has been observed to be able to be stored for up to 21 days in air storage at 21° C.

Market use: The variety was selected for dessert use and because of the very firm flesh has excellent shipping and handling attributes.

Pollination requirements: The variety is diploid and is self fertile.

Pest and disease resistance: Although no specific testing for pest and disease resistance has been undertaken, the variety has not manifested any undue susceptibility to pest and disease.

Plant hardiness: The variety has been observed to be winter hardy under New Zealand conditions, and has not manifested any susceptibility to heat intolerance. Typically New Zealand summer conditions do not exceed temperatures in the range to 30° C.

We claim:

1. A new and distinct peach tree substantially as herein described and illustrated characterized by late flowering, vigorous spreading growth; regular and heavy cropping of large, very firm, white-fleshed crisp-textured fruit which are clingstone with mild and sweet sub-acid flavor and fruit aroma, the fruit being further characterized by pink overcolour and very good handling qualities.

* * * * *

UNITED STATES PATENT AND TRADEMARK OFFICE

CERTIFICATE OF CORRECTION

PATENT NO. : PP 14,347 P3
DATED : December 2, 2003
INVENTOR(S) : Malone et al.

It is certified that error appears in the above-identified patent and that said Letters Patent is hereby corrected as shown below:

Column 2,
Line 5, delete "mid" and replace with -- late --.

Column 3,
Line 1, delete "one" with -- once --.
Line 58, in the discussion of "*Sepals,*" insert -- diameter, -- before the word "approximately."

Signed and Sealed this

Twenty-fourth Day of February, 2004

JON W. DUDAS
*Acting Director of the United States Patent and Trademark Office*